United States Patent
Walter et al.

(10) Patent No.: US 9,873,645 B2
(45) Date of Patent: Jan. 23, 2018

(54) METHOD FOR PRODUCING HYDROCARBON PRODUCTS

(71) Applicant: Linde Aktiengesellschaft, Munich (DE)

(72) Inventors: Stefanie Walter, Seehausen (DE); Helmut Fritz, Munich (DE); Gunther Schmidt, Deisenhofen (DE)

(73) Assignee: Linde Aktiengesellschaft, München (DE)

( * ) Notice: Subject to any disclaimer, the term of this patent is extended or adjusted under 35 U.S.C. 154(b) by 0 days.

(21) Appl. No.: 14/916,161

(22) PCT Filed: Sep. 3, 2014

(86) PCT No.: PCT/EP2014/068708
§ 371 (c)(1),
(2) Date: Mar. 2, 2016

(87) PCT Pub. No.: WO2015/032804
PCT Pub. Date: Mar. 12, 2015

(65) Prior Publication Data
US 2016/0194259 A1    Jul. 7, 2016

(30) Foreign Application Priority Data

Sep. 5, 2013 (DE) .................. 10 2013 014 866
Sep. 25, 2013 (EP) .................... 13004662

(51) Int. Cl.

| | |
|---|---|
| C07C 4/04 | (2006.01) |
| C10G 45/58 | (2006.01) |
| C10G 65/04 | (2006.01) |
| C10G 69/06 | (2006.01) |
| C10G 70/04 | (2006.01) |
| C10G 9/36 | (2006.01) |
| C07C 5/13 | (2006.01) |
| C07C 5/333 | (2006.01) |
| C07C 7/148 | (2006.01) |
| C07C 5/03 | (2006.01) |
| C07C 41/06 | (2006.01) |
| C07C 41/34 | (2006.01) |

(52) U.S. Cl.
CPC ............. *C07C 4/04* (2013.01); *C07C 5/03* (2013.01); *C07C 5/13* (2013.01); *C07C 5/333* (2013.01); *C07C 7/14891* (2013.01); *C07C 41/06* (2013.01); *C07C 41/34* (2013.01); *C10G 9/36* (2013.01); *C10G 45/58* (2013.01); *C10G 65/04* (2013.01); *C10G 69/06* (2013.01); *C10G 70/041* (2013.01); *C10G 2300/104* (2013.01); *C10G 2300/20* (2013.01); *C10G 2300/4081* (2013.01)

(58) Field of Classification Search
CPC ........... C07C 4/04; C07C 41/06; C07C 41/34; C07C 5/03; C07C 5/13; C07C 5/333; C07C 7/14891; C10G 45/58; C10G 65/04; C10G 69/06; C10G 70/041; C10G 9/36
See application file for complete search history.

(56) References Cited

U.S. PATENT DOCUMENTS

| | | | |
|---|---|---|---|
| 3,922,216 A | 11/1975 | Wilson et al. | |
| 4,091,046 A | 5/1978 | Dixon | |
| 5,523,502 A | 6/1996 | Rubin | |
| 2011/0112345 A1* | 5/2011 | Chewter | ............... C01B 3/22 585/302 |

FOREIGN PATENT DOCUMENTS

EP    2062865 A1    5/2009

OTHER PUBLICATIONS

Translation of the International Preliminary Report on Patentability corresponding to International Patent Application No. PCT/EP2014/068708, mailed Mar. 17, 2016, 8 pages.

* cited by examiner

*Primary Examiner* — Pancham Bakshi
*Assistant Examiner* — Mark Luderer
(74) *Attorney, Agent, or Firm* — Lathrop Gage LLP

(57) ABSTRACT

The invention relates to a method for producing hydrocarbon products which comprises preparing a hydrocarbon stream (C4) which predominantly comprises branched and unbranched hydrocarbons each having four carbon atoms. A first and a second partial stream (i-C4, n-C4) are obtained from this stream (C4), the first partial stream (i-C4) predominantly comprising branched hydrocarbons with four carbon atoms and the second partial stream (n-C4) predominantly comprising unbranched hydrocarbons with four carbon atoms. The method further comprises the steam cracking of at least part of the first partial stream (i-C4) at a first, higher cracking severity and at least part of the second partial stream (n-C4), at a second, lower, cracking severity.

12 Claims, 2 Drawing Sheets

METHOD FOR PRODUCING HYDROCARBON PRODUCTS

The invention relates to a method and an apparatus for producing hydrocarbon products according to the precharacterising clauses of the independent claims.

PRIOR ART

Methods and apparatus for steam cracking hydrocarbons are known and are described for example in the article "Ethylene" in Ullmann's Encyclopedia of Industrial Chemistry, online since 15 Apr. 2007, DOI 10.1002/14356007.a10_045.pub2.

EP 2 062 865 A1 discloses a method for the selective preparation of ethylene, propylene and isoprene from light hydrocarbons, which comprises separating a butane fraction into a fraction enriched in iso-butane and a fraction enriched in n-butane, and processing the fraction enriched in n-butane, optionally together with other fractions, by steam cracking.

A method of preparing iso-amylene from iso-butane is known from U.S. Pat. No. 4,091,046 A. US 2011/0112345 A1 discloses a method of preparing an olefin product which comprises ethylene and/or propylene, in which a paraffinic feedstock is processed by steam cracking. Methods of treating hydrocarbon streams are also known from U.S. Pat. Nos. 5,523,502 A, 4,324,938 A and FR 2 436 176 A1.

In more recent steam cracking methods and apparatus, mild cracking conditions are increasingly used (see below), because these produce in particular so-called high value products, for example propylene and butadiene, in improved yields, as explained hereinafter. However, at the same time, the conversion of the furnace feed is decreased under mild cracking conditions, with the result that compounds contained therein are found in the cracking gas in comparatively large amounts and lead to "dilution" of the high value products.

The problem of the invention is to remedy this and to retain the advantages of the mild cracking conditions while avoiding the disadvantages. In particular, by reducing the diluting effect mentioned above, the concentration and quantity of the high value products, particularly 1,3-butadiene, should be increased.

DISCLOSURE OF THE INVENTION

This problem is solved by a method and an apparatus for producing hydrocarbon products having the features of the independent claims. Preferred embodiments are the subject of the dependent claims and of the description that follows.

Before the features and advantages of the present invention are described, their basis and the terminology used will be explained.

Steam cracking processes are carried out on a commercial scale almost exclusively in tubular reactors in which individual reaction tubes (in the form of coiled tubes, so-called coils) or groups of corresponding reaction tubes can also be operated under different cracking conditions. Reaction tubes or sets of reaction tubes and also tubular reactors operated under uniform cracking conditions are hereinafter referred to as "cracking furnaces" in each case. A cracking furnace, in the terminology used herein, is thus a constructive unit used for steam cracking which exposes a furnace feed to identical or comparable cracking conditions. A steam cracking apparatus may comprise one or more cracking furnaces of this kind.

The term "furnace feed" as used herein denotes one or more liquid and/or gaseous streams which are fed into one or more cracking furnaces. Also, streams obtained by a corresponding steam cracking process as explained hereinafter may be recycled into one or more cracking furnaces and used again as a furnace feed. A large number of hydrocarbons and hydrocarbon mixtures from ethane to gas oil up to a boiling point of typically 600° C. are suitable as furnace feeds.

A furnace feed may consist of a so-called "fresh feed", i.e. a feed which is prepared outside the apparatus and is obtained for example from one or more petroleum fractions, petroleum gas components with two to four carbon atoms and/or petroleum gas condensates. A furnace feed may also consist of one or more so-called "recycle streams", i.e. streams that are produced in the apparatus itself and are recycled into a corresponding cracking furnace. A furnace feed may also consist of a mixture of one or more fresh feeds with one or more recycle streams.

The furnace feed is at least partly converted in the respective cracking furnace and leaves the cracking furnace as a so-called "raw gas", which, as explained hereinafter with reference to FIGS. 1A and 1B, may be subjected to a series of after-treatment steps. These after-treatment steps encompass, first of all, processing of the raw gas, for example by quenching, cooling and drying, so as to obtain a so-called "cracking gas". Occasionally, already the raw gas is referred to as cracking gas.

Current methods include in particular the separation of the cracking gas into a number of fractions based on the different boiling points of the components obtained. In the art, abbreviations are used for these which indicate the carbon number of the hydrocarbons that are predominantly or exclusively contained. Thus, a "C1 fraction" is a fraction which predominantly or exclusively contains methane (but according to convention also contains hydrogen in some cases, then also called "C1minus fraction"). A "C2 fraction" on the other hand predominantly or exclusively contains ethane, ethylene and/or acetylene. A "C3 fraction" predominantly contains propane, propylene, methylacetylene and/or propadiene. A "C4 fraction" predominantly or exclusively contains butane, butene, butadiene and/or butyne, while the respective isomers may be present in different amounts depending on the source of the C4 fraction. The same also applies to a "C5 fraction" and the higher fractions. Several such fractions may also be combined in one process and/or under one heading. For example, a "C2plus fraction" predominantly or exclusively contains hydrocarbons with two or more carbon atoms and a "C2minus fraction" predominantly or exclusively contains hydrocarbons with one or two carbon atoms.

Liquid and gaseous streams may, in the terminology as used herein, be rich in or poor in one or more components, "rich" indicating a content of at least 90%, 95%, 99%, 99.5%, 99.9%, 99.99% or 99.999% and "poor" indicating a content of at most 10%, 5%, 1%, 0.1%, 0.01% or 0.001% on a molar, weight or volume basis. The term "predominantly" denotes a content of at least 50%, 60%, 70%, 80% or 90% or corresponds to the term "rich". Liquid and gaseous streams may also, in the terminology as used herein, be enriched or depleted in one or more components, these terms relating to a corresponding content in a starting mixture from which the liquid or gaseous stream was obtained. The liquid or gaseous stream is "enriched" if it contains at least 1.1 times, 1.5 times, 2 times, 5 times, 10 times, 100 times or 1,000 times the amount, "depleted" if it contains at most 0.9 times, 0.5 times, 0.1 times, 0.01 times or 0.001 times the amount of a corresponding component, based on the starting mixture. A stream "derived" from a corresponding starting stream may be formed for example by branching off or separating from the starting stream or by combining with at least one other stream.

The "cracking conditions" mentioned in a cracking furnace encompass inter alia the partial pressure of the furnace feed, which may be influenced by the addition of different amounts of steam and the pressure selected in the cracking furnace, the dwell time in the cracking furnace and the temperatures and temperature profiles used therein. The furnace geometry and configuration also play a part. To produce ethylene a cracking furnace is operated for example at a furnace entry temperature of 500 to 680° C. and at a furnace exit temperature of 775 to 875° C. The "furnace entry temperature" is the temperature of a gas stream at the start of a reaction tube and the "furnace exit temperature" is the temperature of a gas stream at the end of a reaction tube. Typically, the latter is the maximum temperature to which the gas stream in question is heated. It is mixed with the furnace feed at a pressure of 165 to 225 kPa, measured at the furnace exit, in a ratio of typically 0.25 to 0.85 kg/kg. The values specifically used are dependent on the particular furnace feed used and the desired cracking products.

As the values mentioned influence one another at least partially, the term "cracking severity" has been adopted to characterise the cracking conditions. For liquid furnace feeds the cracking severity can be described by means of the ratio of propylene to ethylene (P/E) or as the ratio of methane to propylene (M/P) in the cracked gas, based on weight (kg/kg). The P/E and M/P ratios are directly dependent on the temperature, but, unlike the real temperature in or at the exit from a cracking furnace, they can be measured much more accurately and be used for example as a control variable in a corresponding regulating process. The P/E ratio is, however, only of limited use in characterising the cracking severity in gaseous furnace feeds or in compounds with two to four carbon atoms.

For gaseous furnace feeds the reaction or conversion of a particular component of the furnace feed may be specified as a measure of the cracking severity. The term reaction or conversion is used in the manner conventional in the art (cf. for example the above-mentioned article "Ethylene" in Ullmann's Encyclopedia of Industrial Chemistry). In particular, for the C4 fractions or C4 partial streams used in the present case, it is useful to describe the cracking severity in terms of the conversion of key components such as n-butane and iso-butane.

The cracking severities or cracking conditions are "severe" if n-butane in a corresponding fraction is converted by more than 92%. Under even more severe cracking conditions, n-butane is optionally converted by more than 93%, 94% or 95%. Typically, there is no 100% conversion of n-butane. The upper limit of the "severe" cracking severities or cracking conditions is therefore 99%, 98%, 97% or 96% conversion of n-butane, for example. The cracking severities or cracking conditions are "mild", on the other hand, if n-butane is converted by less than 92%. At less than 91%, less than 90%, less than 89%, less than 88% or less than 87% conversion of n-butane, ever milder cracking severities or cracking conditions are present. At less than 86% conversion of n-butane the cracking severities or cracking conditions are referred to as "very mild". Very mild cracking severities or cracking conditions also encompass, for example, a conversion of n-butane of less than 85%, 84%, 83%, 82%, 81%, 80%, 79%, 78%, 77%, 76%, 75%, 70% or 65% and more than 50% or 60%.

The cracking severities or cracking conditions are also "severe" when iso-butane in a corresponding fraction is converted by more than 91%. Under even more severe cracking conditions iso-butane is optionally converted by more than 92%, 93% or 94%. Typically, there is no 100% conversion of iso-butane either. The upper limit of the "severe" cracking severities or cracking conditions is therefore at 99%, 98%, 97% or 96% conversion of iso-butane, for example. The cracking severities or the cracking conditions are, however, "mild" if iso-butane is converted by less than 91%. At less than 90%, less than 89%, less than 88%, less than 87% or less than 86% conversion of iso-butane, milder cracking severities or cracking conditions are increasingly obtained. At less than 83% conversion of iso-butane the cracking severities or cracking conditions are referred to here as "very mild". Very mild cracking severities or cracking conditions also include for example a conversion of iso-butane of less than 82%, 81%, 80%, 79%, 78%, 77%, 76%, 75% or 70% and more than 45% or 50%.

The above-mentioned cracking severities or cracking conditions are correlated in particular with the furnace exit temperature at the end of the reaction tube or cracking furnaces used, as described above. The higher this temperature, the more "severe", and the lower the temperature, the "milder" the cracking severities or cracking conditions.

It should also be understood that the conversion of other components does not have to be identical to that of n- and iso-butane. If, for example, 1- and 2-butene are cracked together with n-butane, these are typically conversion to a greater extent than n-butane. Conversely, iso-butene is converted to a lesser extent than iso-butane, if it is cracked together with the latter. A percentage conversion of a key component, in this case n-butane or iso-butane, is therefore associated with a furnace exit temperature and the respective percentage conversions of the other components in the feedstock. This furnace exit temperature is in turn dependent on the cracking furnace, among other things. The difference between the respective percentage conversions is dependent on a number of other factors.

Advantages of the Invention

The present invention starts from a method for producing hydrocarbon products in which a hydrocarbon stream is provided which predominantly comprises branched and unbranched hydrocarbons with four carbon atoms (hereinafter also referred to as C4 fraction or C4 stream, abbreviated to C4). To this extent the method according to the invention corresponds for example to known methods of producing hydrocarbon products by steam cracking, in which a C4 fraction of this kind is separated from a cracking gas which has been processed accordingly. This may take place in known apparatus in a so-called debutanizer (although this also separates all the other hydrocarbons with four carbon atoms from a corresponding hydrocarbon stream). Details of this are shown in the above-mentioned article "Ethylene" in Ullmann's Encyclopedia of Industrial Chemistry and illustrated with reference to FIGS. 1A and 1B.

However, the invention is not restricted to the use of C4 streams provided by steam cracking and subsequent process steps, but is equally suitable for C4 streams produced at least partly using other methods, for example by refinery processes. For example, the invention may be used with C4 streams which have not been steam-cracked beforehand and are only subsequently fed into a corresponding steam cracking process. These may be, for example, petroleum fractions, petroleum gas components with two to four carbon atoms, petroleum gas condensates and the like.

It is now provided, according to the invention, that a first and a second partial stream be obtained from the above-mentioned hydrocarbon stream which predominantly comprises branched and unbranched hydrocarbons with four carbon atoms, the first partial stream predominantly comprising branched hydrocarbons with four carbon atoms and the second partial stream predominantly comprising unbranched hydrocarbons with four carbon atoms. The first partial stream is hereinafter also referred to as the iso-C4 fraction or iso-C4 stream (abbreviated to iso-C4), the second partial stream is also referred to as the n-C4 fraction or n-C4 stream (n-C4).

It is further provided according to the invention that at least part of the first partial stream or a stream derived therefrom be cracked at a first, higher cracking severity and at least part of the second partial stream or a stream derived therefrom be cracked at a second, lower cracking severity, the first, higher cracking severity resulting in a conversion of iso-butane in the first partial stream of more than 91% and up to 99% and the second, lower cracking severity resulting in a conversion of n-butane in the second partial stream of less than 92% and more than 50%. The "cracking" involves feeding the corresponding partial stream (or a corresponding proportion thereof) on its own or together with other streams, optionally after previous combining into a combined stream, into a cracking furnace as defined hereinbefore and removing a cracking gas from the cracking furnace.

The terms "higher" and "lower" used to define the cracking severity relate to one another. In other words, at least part of the first partial stream is cracked at a first cracking severity and at least part of the second partial stream is cracked at a second cracking severity, the first cracking severity being higher than the second and the second being lower than the first.

The steam cracking of C4 fractions of different origins is known in the art. The cracking results can be reliably predicted with the tools available. As a rule, they are present as mixtures of branched and unbranched C4-compounds. In the fresh feeds mentioned previously, these predominantly comprise paraffinic compounds, while in recycling streams from steam cracking processes or in products of other treatment processes (e.g. from refineries) they predominantly comprise olefinic compounds.

Particularly when cracking naphthas under mild cracking conditions or with a high proportion of C4 fresh feeds, the proportion of C4 fraction obtained from the corresponding cracking gas is also great and in particular has a relatively low concentration of 1,3-butadiene and optionally other high value products which are to be extracted from the C4 fraction. As a result, the recovery of 1,3-butadiene is uneconomical.

Particularly when steam cracking hydrocarbons under unusually mild cracking conditions there is thus a substantial increase in the amount of some product fractions, as already mentioned, and a consequent reduction in the concentration of high value products present (dilution effect). This makes the recovery of the high value products more difficult or more expensive.

The invention is based on the finding that branched C4 compounds in the cracking furnace contribute to the formation of 1,3-butadiene to a minor extent by reason of their structure. A relatively high methane formation from such compounds is unavoidable, particularly when the branched C4 compounds are recycled until fully converted. Thus, if C4 mixtures are cracked under mild or even very mild conditions, this results in C4 fractions of relatively large mass flows with, at the same time, a low concentration of 1,3-butadiene.

This effect is countered according to the invention by separating the C4 fraction into iso- and n-C4 partial streams (the first and second partial stream mentioned above) before the steam cracking, for example by distillation, and cracking them under different conditions. The (first) iso-C4 partial stream is cracked more severely than the (second) n-C4 partial stream, the (first) iso-C4 partial stream especially being cracked particularly severely and the (second) n-C4 partial stream especially being cracked particularly mildly.

Thanks to the invention, the disadvantages of mild cracking are reduced or eliminated completely, while retaining its advantages, i.e. the amount of C4 fraction is reduced and as a result the concentration of the target product, in this case particularly 1,3-butadiene, is increased. The specific extraction costs are reduced.

The core of the invention is therefore the minimising of the C4 fraction as a whole by a controlled increase in the structural conversion of iso-C4 compounds by severe cracking conditions after previous separation of n-C4 compounds. In this way the selective use of mild, particularly very mild cracking conditions on the n-C4 compounds is made possible, so as to obtain the high selectivities which can be achieved in this way, e.g. towards 1,3-butadiene.

It is particularly advantageous if the first partial stream, i.e. the one predominantly comprising branched hydrocarbons with four carbon atoms, is at least partially subjected to a hydrogenation process before the steam cracking at the first, higher cracking severity. During this process the iso-butene present (olefinic) is reacted at least partially to form iso-butane (paraffinic). Within the scope of the present invention it has been found that in the subsequent cracking process, i.e. at the first, higher cracking severity, the iso-butane can be reacted more easily, or to form more easily utilisable products. This makes it possible to reduce the quantity of the C4 fraction still further and thereby concentrate the target products, as mentioned hereinbefore.

For hydrogenating olefins or olefin-containing hydrocarbon mixtures, numerous catalytic methods are known from the prior art, which can also be used within the scope of the present invention. Hydration catalysts have, as a hydrogenation-active component, one or more elements of the $6^{th}$, $7^{th}$ or $8^{th}$ sub-group of the Periodic Table in elemental or bound form. They may be doped with different additives in order to influence specific catalyst properties, for example service life, resistance to specific catalyst poisons, selectivity or regenerability. The hydrogenation catalysts often contain the hydrogenation-active components on supports, for example mordenites, zeolites, $Al_2O_3$ modifications, $SiO_2$ modifications and so on. Generally, reaction temperatures of 150 to 250° C. are used for the extensive hydrogenation of the olefins.

The process variants described above may encompass at least partially forming the above-mentioned hydrocarbon stream, from which the first and the second partial stream are obtained, from at least one cracking gas stream which is produced during the steam cracking according to the invention of the first and second partial streams or corresponding proportions thereof together with fresh feed.

However, the hydrocarbon stream may also be formed at least partly from a cracking gas which is obtained by steam cracking a fresh feed, or from an uncracked fresh feed. These alternatives make it possible to achieve a very flexible adjustment of the desired content of the hydrocarbon stream in terms of the individual C4 compounds.

According to the invention, the first, higher cracking severity, which is used for the iso-C4 compounds, results in a conversion of the iso-butane present of at least 91% or more, as explained above on the subject of the cracking severity. Thus, for the iso-C4 compounds, severe or very severe cracking severities or cracking conditions are used. These may also correspond for example to more than 92%, 93% or 94% and up to 99% conversion of iso-butane. The second, lower, cracking severity which is used for the n-C4 compounds, by contrast advantageously results in a conversion of the n-butane present of at most 92% or less, as also explained above. Thus, for the n-C4 compounds, mild or very mild cracking severities or cracking conditions are used. These may for example also correspond to less than 90%, 88%, 86%, 84%, 82%, 80%, 78%, 76%, 74%, 72%, 70% or 65%, but more than 50% or 60% conversion of n-butane, for example. At increasingly mild cracking conditions, in relation to the fresh feed, more of the desired products such as butadiene and propylene are obtained, so that the yield is increased and the product spectrum is improved.

The cracking severities, meanwhile, differ by 1 to 20%, particularly by 2 to 20%, standardised to a common basic value, for example a conversion of n-butane or iso-butane or both.

Corresponding methods advantageously comprise the use of a quantity of steam of 0.4 kg/kg, particularly 0.2 to 0.7 kg/kg, for example 0.3 to 0.5 kg/kg at the first, higher cracking severity and the use of a quantity of steam of 0.4 kg/kg, particularly 0.2 to 0.7 kg/kg, for example 0.3 to 0.5 kg/kg at the second, lower cracking severity. The values used may be identical or different and in particular may also be adapted to other cracked feeds.

The method according to the invention proves particularly advantageous when the steam cracking at the first, higher cracking severity and/or the steam cracking at the second, lower cracking severity is carried out in each case in at least one cracking furnace which is supplied with at least one other furnace feed. For example, a cracking furnace designed for a corresponding throughput may be used which is operated at the second, lower cracking severity and in which, besides the second partial stream containing the n-C4 compounds, a "regular" fresh feed is also mildly cracked. The iso-C4 compounds may be cracked on their own in a cracking furnace. In certain cases, however, for example when similar cracking furnaces are used for reasons of cost, it may be more sensible to crack the iso-C4 compounds severely, together with a fresh feed.

As mentioned above, the particular purpose of the present invention is to improve a method in which 1,3-butadiene is separated from the hydrocarbon stream. All the known methods for extracting 1,3-butadiene are suitable for this purpose.

Other advantages may be obtained if, after separation of the 1,3-butadiene, isobutene contained in the hydrocarbon stream is at least partly reacted to form a tert-butylether and this is also extracted. The preparation of methyl-tert-butylether (2-methoxy-2-methylpropane, MTBE) is known in principle. MTBE is produced industrially with acid catalysis from isobutene and methanol, which is added to the hydrocarbon stream. MTBE is mainly used as an anti-knocking agent, but is also increasingly used as a solvent and extraction agent in organic chemistry. Ethanol yields ethyl-tert-butylether. Other alcohols may also be used.

Also advantageous is a method in which 1-butene contained in the hydrocarbon stream is at least partially hydroisomerised to 2-butene after the at least partial reaction of the isobutene. The 2-butene obtained can be reacted particularly selectively in the subsequent mild cracking to produce the desired butadiene. Corresponding hydroisomerisation methods are also known. For example, any residual traces of butadiene can also be eliminated in this way.

It may also be advantageous to feed at least one other stream, particularly a stream containing a butyne (C4-acetylene) and/or hydrocarbons with five carbon atoms, into the C4-hydrocarbon stream which comprises predominantly branched and unbranched hydrocarbons each having four carbon atoms, before or after the hydroisomerisation or another process. For example, C5 compounds coextracted during a butadiene extraction may be utilised and thus put to good use.

The invention is hereinafter explained relative to the prior art with reference to the appended Figures.

BRIEF DESCRIPTION OF THE DRAWINGS

In the Figures, corresponding elements have been given identical reference numerals and are not explained repeatedly, in the interests of clarity.

DETAILED DESCRIPTION OF THE DRAWINGS

Figure 1A:
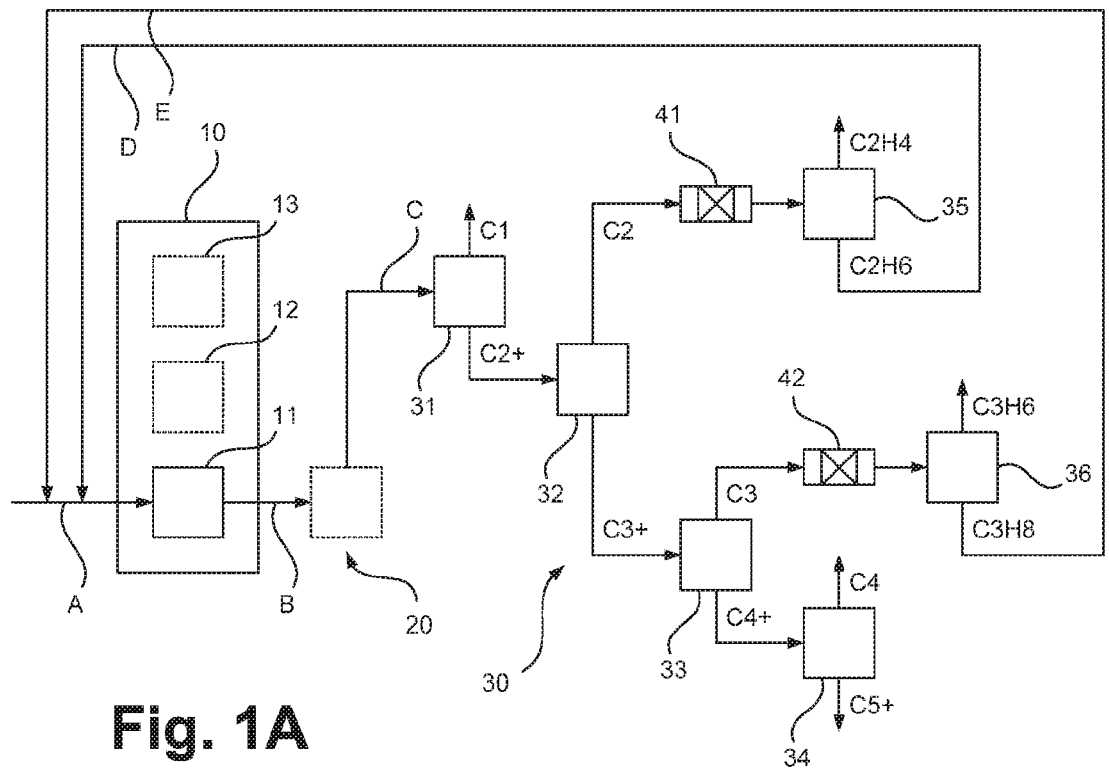
FIG. 1A schematically shows the course of a process for producing hydrocarbons according to the prior art.

FIG. 1A shows the course of a method of producing hydrocarbons according to the prior art in the form of a schematic flow diagram. The core of the method here is a steam cracking process 10 which can be carried out using one or more cracking furnaces 11 to 13. Only the operation of the cracking furnace 11 is described hereinafter; the other cracking furnaces 12 and 13 may operate in a corresponding manner.

The cracking furnace 11 is charged with a stream A as the furnace feed, and this may be at least partially a so-called fresh feed which is provided from sources outside the apparatus, and at past partially a so-called recycle stream which is obtained in the method itself, as explained below. The other cracking furnaces 12 and 13 may also be charged with corresponding streams. Different streams may also be fed into different cracking furnaces 11 to 13, one stream may be divided between several cracking furnaces or several partial streams may be combined to form one combined stream which is fed for example as stream A into one of the cracking furnaces 11 to 13.

As a result of steam cracking in the steam cracking process 10 a raw gas stream B is obtained which is occasionally already at this point referred to as a cracking gas stream. The raw gas stream B is prepared in a series of preparation stages (not shown) of a preparation process 20, subjected to a so-called oil quench, for example, prefractionated, compressed, cooled further and dried.

Figure 1B:
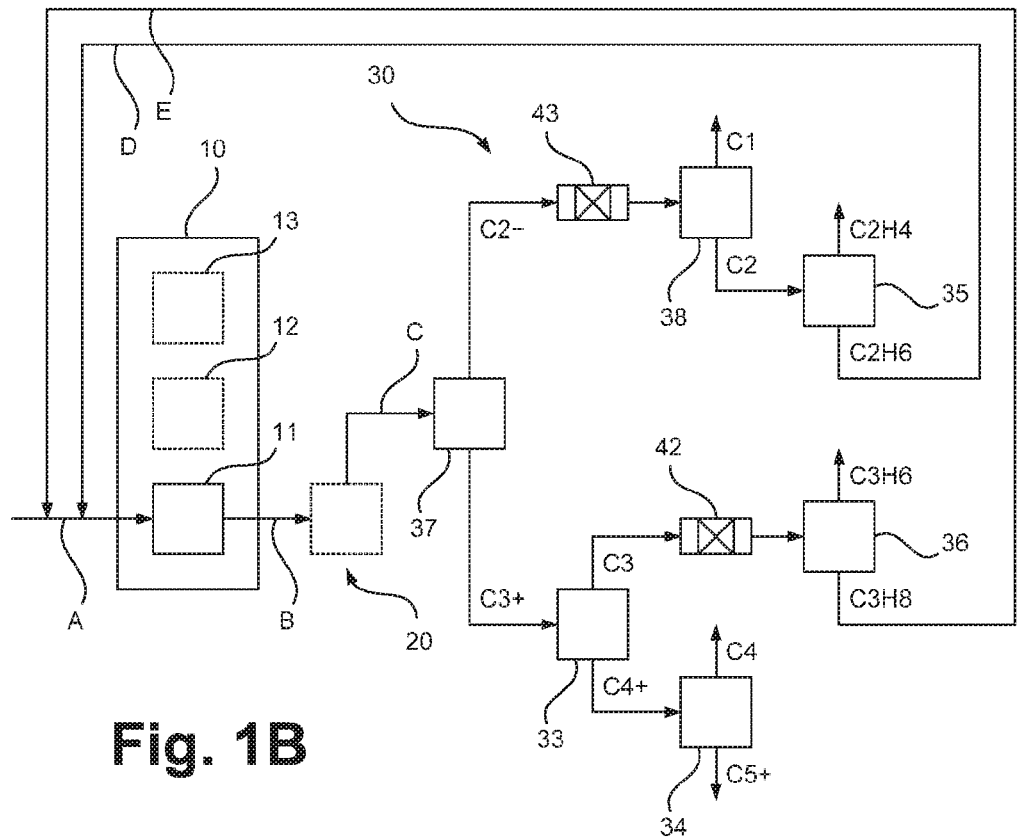
FIG. 1B schematically shows the course of a process for producing hydrocarbons according to the prior art.

The correspondingly treated stream B, the actual cracking gas C, is then subjected to a separation process 30. In this process a number of fractions are obtained which, as explained hereinbefore, are named according to the carbon number of the hydrocarbons that they predominantly contain. The separation process 30 shown in FIG. 1A operates according to the principle of "Demethanizer First", a separation process according to the principle of "Deethanizer First" is shown in FIG. 1B.

In the separation process 30 a C1– or C1minus fraction (designated C1) which may also contain hydrogen, unless it has already been removed beforehand, is first separated in gas form from the cracking gas C in a first separating unit 31 (the so-called demethanizer). It is typically used as a combustion gas. A liquid C2plus fraction (reference numeral C2+) remains which is transferred into a second separating unit 32 (the so-called Deethanizer).

In the second separating unit 32 a C2 fraction (reference numeral C2) is separated off in gaseous form from the C2plus fraction and subjected for example to a hydrotreatment process 41 in order to convert any acetylene present to ethylene. Then the C2 fraction is separated in a C2 separating unit 35 into ethylene (reference numeral C2H4) and ethane (reference numeral C2H6). The latter can be subjected to the steam cracking process 10 again as a recycle stream D in one or more cracking furnaces 11 to 13. In the example shown the recycle streams D and E are added to the stream A. The recycle streams D and E and the stream A can also be fed into different cracking furnaces 11 to 13.

In the second separating unit 32 a liquid C3plus fraction (reference numeral C3+) remains, which is transferred into a third separating unit 33 (the so-called depropanizer). In the third separating unit 33 a C3 fraction (reference numeral C3) is separated from the C3plus fraction and subjected to another hydrotreatment process 42, to convert the propylene contained in the C3 fraction into propene. Then the C3 fraction is separated in a C3 separating unit 36 into propene (reference numeral C3H6) and propane (reference numeral C3H8). The latter may be subjected to the steam cracking process 10 once more as recycle stream E in one or more cracking furnaces n to 13, separately or with other streams.

In the third separating unit 33 a liquid C4plus fraction (reference numeral C4+) accordingly remains, which is transferred into a fourth separating unit 34 (the so-called Debutanizer). In the fourth separating unit 34 a C4 fraction (reference numeral C4) is separated from the C4plus fraction. A liquid C5plus fraction remains (reference numeral C5+).

It will be understood that all the fractions described can also be subjected to suitable after-treatment steps. For example, 1,3-butadiene may be separated from the C4 fraction, as described below. Also, additional recycle streams may be used which may be subjected to the steam cracking process 10 analogously to the recycle streams D and E.

FIG. 1B shows the course of an alternative method of producing hydrocarbons by steam cracking according to the prior art in the form of a schematic flow diagram. Once again, the core of the method is a steam cracking process 10 which may be carried out using one or more cracking furnaces 11 to 13. In contrast to the method shown in FIG. 1A the cracking gas C here is subjected to an alternative separation process 30 according to the principle of "Deethanizer First".

In the separation process 30 a C2minus fraction (reference numeral C2–), which may predominantly contain methane, ethane, ethylene and acetylene and, if it has not already been eliminated, hydrogen as well is first separated in gaseous form from the cracking gas C in a first separating unit 37. The C2minus fraction as a whole is subjected to a hydrotreatment process 43, to convert acetylene into ethylene. Then a C1 fraction is separated from the C2minus fraction in a C2minus separating unit 38 and further used as described above. A C2 fraction remains which is separated in a C2 separating unit 35 as above into ethylene and ethane. The latter may be subjected again to the steam cracking process 10 as a recycle stream D in one or more cracking furnaces 11 to 13. In the first separating unit 37 a liquid C3plus fraction remains which is treated in the separating units 33 to 36 and the hydrotreatment unit 42, as explained with reference to FIG. 1.

The skilled man will be familiar with numerous other process variants, for example from the article "Ethylene" in Ullmann's Encyclopedia of Industrial Chemistry mentioned hereinbefore, which differ in the preparation of the cracking gas C and/or the separation process used.

The C4 fraction may also be subjected to the steam cracking process 10 again in parts as a corresponding recycle stream in one or more of the cracking furnaces 11 to 13. Particularly when mild cracking conditions are used, however, branched C4 compounds (iso-C4 compounds) contained in the C4 fraction may be converted to a lesser extent than n-C4 compounds and are therefore once again found to a large extent in the cracking gas stream C. The iso-C4 compounds are therefore circulated many times through a corresponding apparatus. The consequence of such a mild steam cracking process is thus a significant increase in the amount of some product fractions, in this case the iso-C4 compounds, and a consequent reduction in the concentration of high value products present, such as 1,3-butadiene in this case, as a result of dilution effects. This makes the high value products more difficult and expensive to recover. In other words, the iso-C4 compounds contribute practically nothing to the formation of 1,3-butadiene, by virtue of their structure. The formation of a relative large quantity of largely worthless methane is unavoidable, particularly when the iso-C4 compounds are recycled until completely converted.

Thus, if C4 fractions are cracked with iso-C4 compounds, regardless of their origin, under mild or very mild conditions, this again results in C4 product fractions of relatively large amounts with at the same time a low 1,3-butadiene concentration.

Figure 2:
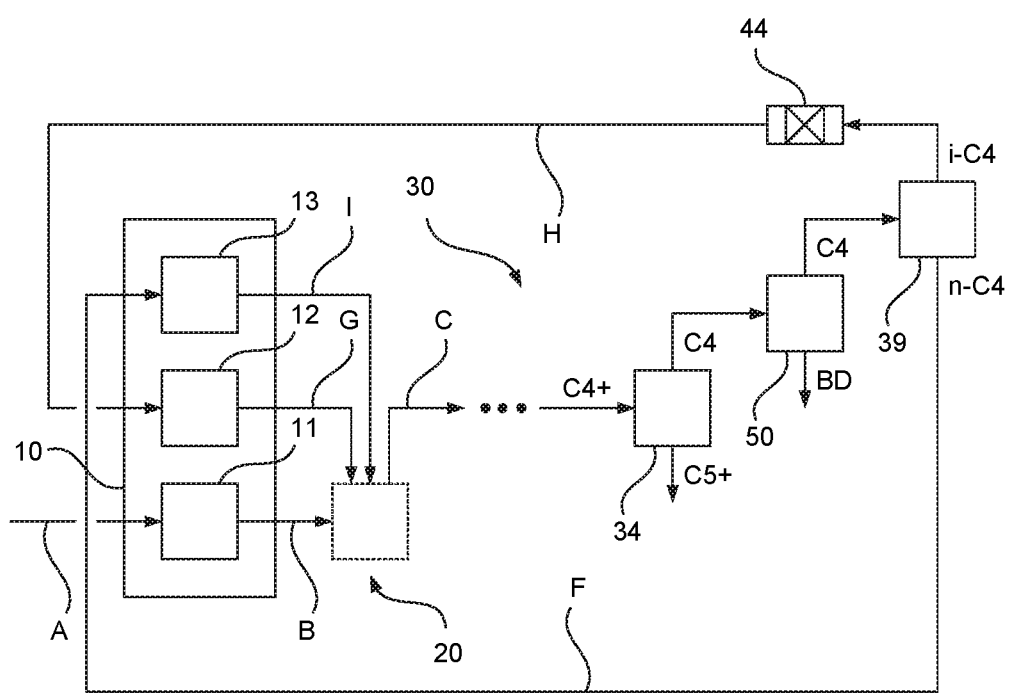
FIG. 2 schematically shows the course of a process for producing hydrocarbons according to one embodiment of the invention.

FIG. 2 shows the course of a method for producing hydrocarbons by steam cracking according to one embodiment of the invention in the form of a schematic flow diagram. Here again, the core of the method is a steam cracking process 10 which may be carried out using cracking furnaces 11 to 13. To illustrate the universal usability of the method shown here, the recovery of a C4plus fraction from the cracking gas C is not shown; however, this may be carried out as shown in FIGS. 1A or 1B or in any other manner known in the art. In the example shown here, the C4plus fraction is supplied to a separating unit 34 which operates as described above. However, if no or only a few C5plus hydrocarbons are formed in a steam cracking process, the use of this separating unit 34 could also be dispensed with. A C4 fraction may, however, also be provided from outside the apparatus, e.g. from a refinery.

A C4 fraction obtained for example from the separating unit 34 may be fed into a 1,3-butadiene recovery unit 50 in which 1,3-butadiene, referred to here as BD, is extracted. Here, 1,3-butadiene represents one of the desired high-value products, the remaining components of the C4 fraction C4 are predominantly of lower economic value and "dilute" the desired 1,3-butadiene, making it more difficult to extract.

According to the embodiment shown, the invention envisages separating iso-C4 and n-C4 compounds (referred to here as i-C4 and n-C4), i.e. branched and unbranched C4 compounds, from one another in a separating unit 39 and recovering corresponding partial streams. The partial stream that predominantly contains the iso-C4 compounds is referred to here as the "first partial stream". This may be recycled as recycle stream H and either subjected once again to the steam cracking process 10 or to another steam cracking process implemented separately from the steam cracking process 10. Preferably, the first partial stream with the iso-C4 compounds is subjected to severe cracking conditions, for which the cracking furnace 12 is designed in this case. Hydrogenation of iso-butene may be carried out beforehand, as illustrated by block 44. A stream G removed from the cracking furnace 12 may be added, for example, to the cracking gas C, optionally after it has also previously been subjected to the preparation process 20.

The partial stream which predominantly contains the n-C4 compounds may be recycled as recycle stream F and once again subjected either to the steam cracking process 10 or to another steam cracking process implemented separately from the steam cracking process 10. Preferably, the n-C4 compounds are subjected to mild to very mild cracking conditions, for which the cracking furnace 13 is designed in this case. Hydrogenation of iso-butene may be carried out beforehand, as illustrated by block 44. A stream G removed from the cracking furnace 12 may be added, for example, to the cracking gas C, optionally after the latter has also previously been subjected to the preparation process 20.

Although not shown here, it will be understood that additional recycle streams or fresh feeds may be supplied to the cracking furnaces 11 to 13.

The invention claimed is:

1. Method for producing hydrocarbon products, which comprises:
    a) preparing a hydrocarbon stream (C4), which predominantly comprises branched and unbranched hydrocarbons each having four carbon atoms, characterised by
    b) recovering a first and a second partial stream (i-C4, n-C4) from the hydrocarbon stream (C4), the first partial stream (i-C4) predominantly comprising branched hydrocarbons with four carbon atoms and the second partial stream (n-C4) predominantly comprising unbranched hydrocarbons with four carbon atoms, and
    c) steam cracking at least a part of the first partial stream (i-C4) or a stream derived therefrom at a first cracking severity and at least a part of the second partial stream (n-C4)) or a stream derived therefrom at a second cracking severity, the first cracking severity resulting in a conversion of iso-butane in the first partial stream of more than 91% and up to 99% and the second cracking severity resulting in a conversion of n-butane in the second partial stream of less than 92% and more than 50%.

2. Method according to claim 1, wherein the first partial stream (i-C4) is at least partially subjected to a hydrogenation process before the steam cracking at the first cracking severity.

3. Method according to claim 1, wherein the hydrocarbon stream (C4) prepared according to a) is at least partially produced from at least one cracking gas (C) obtained by steam cracking according to c).

4. Method according to claim 1, wherein the hydrocarbon stream (C4) prepared according to a) is at least partially produced from a cracking gas (C) which is formed by steam cracking a fresh feed (A).

5. Method according to claim 1, wherein the hydrocarbon stream (C4) prepared according to a) is formed at least partially from an uncracked fresh feed (A).

6. Method according to claim 1, wherein the first cracking severity results in a conversion of iso-butane in the first partial stream of more than 92% and the second cracking severity results in a conversion of n-butane in the second partial stream of less than 90%.

7. Method according to claim 1, wherein the first cracking severity is 1 to 30%, higher than the second cracking severity.

8. Method according to claim 1, wherein the steam cracking at the first cracking severity is carried out using a quantity of steam of 0.2 to 0.7 kg/kg, and the steam cracking at the second cracking severity is carried out using a quantity of steam of 0.2 to 0.7 kg/kg.

9. Method according to claim 1, wherein the steam cracking at the first cracking severity and/or at the second cracking severity is carried out in each case in at least one cracking furnace (12, 13) which is supplied with at least one other furnace feed (A) in the form of at least one recycle stream and/or at least one fresh feed.

10. Method according to claim 1, wherein 1,3-butadiene (BD) is separated from the hydrocarbon stream (C4) before the first and second partial streams (i-C4, n-C4) are recovered according to b).

11. Method according to claim 10, wherein, after the separation of the 1,3-butadiene (BD), isobutene contained in the hydrocarbon stream (C4) is at least partially reacted to form a tert-butylether and the tert-butylether is also separated from the hydrocarbon stream (C4).

12. Method according to claim 11, wherein 1-butene contained in the hydrocarbon stream (C4) is at least partially hydroisomerised to 2-butene.

* * * * *